(12) United States Patent
Melcher

(10) Patent No.: US 7,894,060 B2
(45) Date of Patent: Feb. 22, 2011

(54) MODULAR DUST MEASUREMENT

(75) Inventor: Uwe Melcher, Ottendorf-Okrilla (DE)

(73) Assignee: Sick Engineering GmbH, Ottendorf-Okrilla (DE)

(*) Notice: Subject to any disclaimer, the term of this patent is extended or adjusted under 35 U.S.C. 154(b) by 178 days.

(21) Appl. No.: 12/318,717

(22) Filed: Jan. 7, 2009

(65) Prior Publication Data
US 2009/0180116 A1    Jul. 16, 2009

(30) Foreign Application Priority Data
Jan. 16, 2008   (EP) .................. 08100559

(51) Int. Cl.
*G01N 21/00* (2006.01)
(52) U.S. Cl. ...................... 356/337; 356/338
(58) Field of Classification Search .......... 356/335–343
See application file for complete search history.

(56) References Cited

U.S. PATENT DOCUMENTS 4,890,920 A * 1/1990 Niziolek et al. ............. 356/336

FOREIGN PATENT DOCUMENTS

| DE | 199 46 110 C1 | 2/2001 |
| EP | 0 208 646 A3 | 1/1987 |
| EP | 1 729 107 A1 | 12/2006 |

OTHER PUBLICATIONS

"Staubmessgeräte für die Emissionsüberwachung und Prozesskontrolle" Brochure of SICK | Maihak, 2006.

* cited by examiner

*Primary Examiner*—Michael P Stafira
(74) *Attorney, Agent, or Firm*—The Nath Law Group; Jerald L. Meyer; Stanley N. Protigal

(57) ABSTRACT

A modular dust measuring device (10) is set forth for the determination of a foreign body concentration in a gas having at least one optical sensor head (14) which has a light transmitter (16) and a light receiver (22) and having a central unit (12) which has an evaluation unit (30) and a scavenging air unit (32), wherein the evaluation unit (32) is made to determine the foreign body concentration with the help of a scattered light intensity or transmitted light intensity recorded by the light receiver (22) and the scavenging air unit (32) can supply the sensor head (14) with scavenging air to avoid or eliminate impurities or deposits. In this respect, the sensor head is made as a sensor module (14) and the central unit is made as a central module (12) in that the evaluation unit (30) is made for the evaluation and control of sensor modules (14) of different measurement principles, the sensor module (14) is interchangeably connected to the central module (12) by standardized data interfaces and connections (26, 28) and the scavenging air unit (32) is able to make scavenging air available in the required quantity and with the required effective pressure for the sensor modules (14) of different measurement principles.

10 Claims, 2 Drawing Sheets

MODULAR DUST MEASUREMENT

Figure 1:
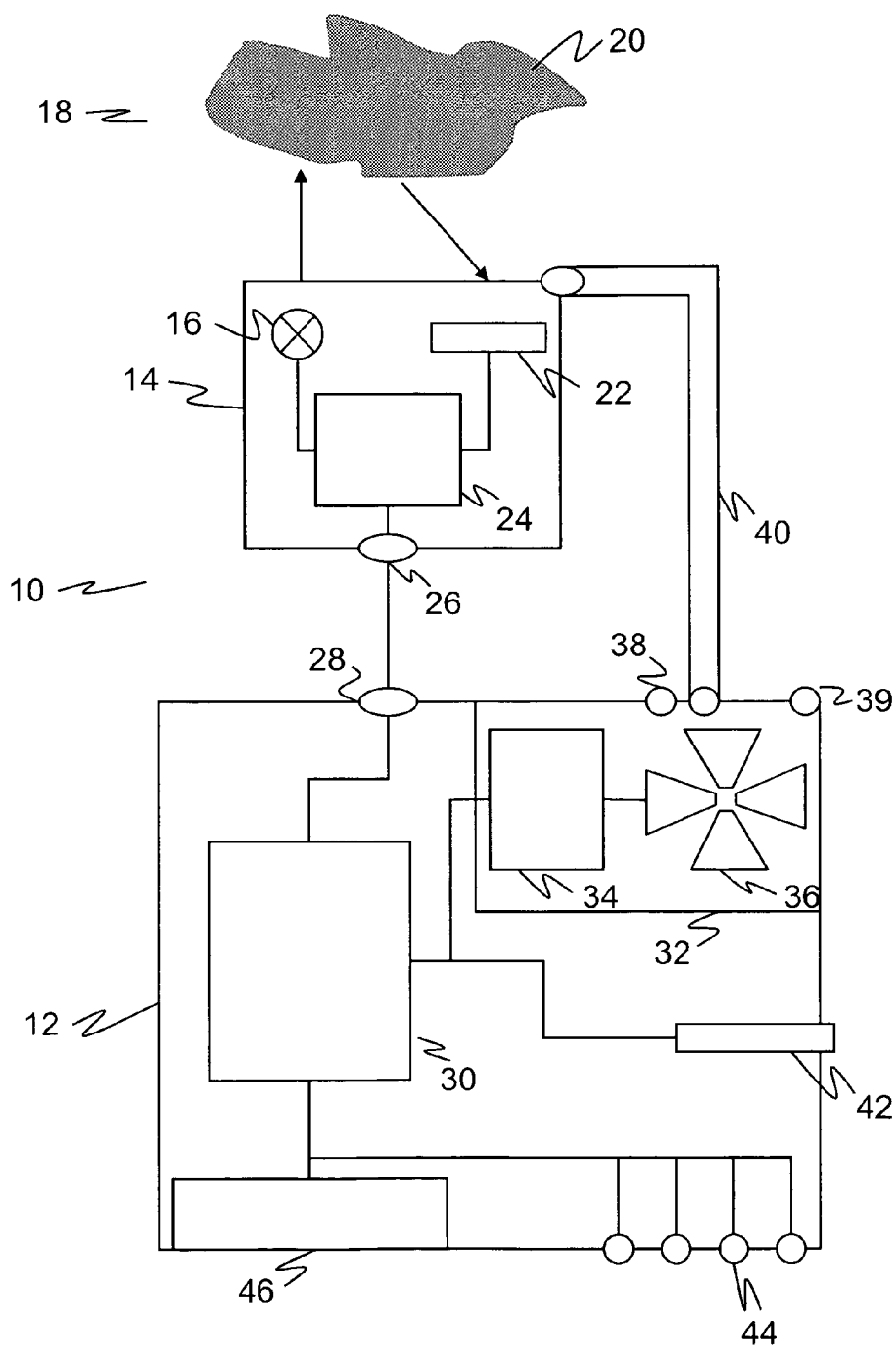

The invention relates to a modular dust measurement device in accordance with the preamble of claim 1 and to a dust measurement method in accordance with the preamble of claim 9.

Optical apparatus for dust measurement are used to determine the concentration of particles (aerosols, dust particles, etc.) in exhaust passages or in the atmosphere. It is thereby possible to determine the sooty particle emission in a chimney, for example. Furthermore, optical apparatus for dust measurement are used in road traffic, in shipping or in aviation to output a warning signal as required when a defined visual range is not reached.

The optical apparatus for dust measurement work either according to the transmission principle or according to the scattered light principle.

In dust measurement according to the transmission principle, a light transmitter transmits a defined light beam into a measurement zone. A reflector which reflects the light beam back through the measurement zone to its starting point is arranged at the oppositely disposed end of the measurement zone. A light reception unit with which the incoming quantity of light is detected is arranged in direct proximity to the light transmitter. Alternatively, the light receiver is located at the oppositely disposed end of the measurement zone instead of the reflector so that measurement light only runs through the measurement stretch once. If there are no particles in the measurement zone, the quantity of light detected by the light reception unit is associated with a transmission value of 100%. The quantity of dust per path stretch can thus be determined from the mathematical relationship between the length of the light path and the transmission value measured in the light reception unit.

The optical apparatus for dust measurement which work according to the principle of scattered light measurement, in contrast to the transmission principle, actually do not evaluate the transmitted portions of light of the light transmitter, but rather the deflected or scattered portions of light of the light transmitter. In this respect, forward scattering and back scattering are distinguished. In back scattering, a light transmitter and a light reception unit are accommodated in a common housing. The transmitted light beam passes through at least one light inlet window and light outlet window into the dust zone; or light coming from the dust zone can reach the light reception unit. The light transmitter and the light reception unit are attached in the common housing such that the light beam transmitted by the light transmitter and the light beam received by the light reception unit overlap within the dust zone. Light will thereby only reach the light reception unit in the scattered light measurement when at least some of the transmitted light beam is scattered back at a particle within the measurement zone. With this principle of backscattered measurement, a quantity of light proportional to the particle frequency thus reaches the light reception unit so that the measurement of the dust concentration is thus possible.

Forward scattering essentially differs by the arrangement of the light receiver which is arranged oppositely disposed in the measurement zone offset by a forward scattering angle to the transmission direction of the light. In this respect, the receiver can be seated in its own housing or, alternatively, in a lance-shaped measurement body which projects into the measurement zone. In forward scattering, the scattered light portion is then evaluated as in back scattering, with the difference that the scattering angle is elongated here and not acute as with back scattering.

Further, non-optical, measurement principles are known, for instance triboelectric measurement or gravimetric measurement. Each of these described measurement principles or the dust measurement device working according to this measurement principle is suitable for specific applications which differ by intensity of dust pollution, water vapor proportion, dimensions of the measurement zones such as of a chimney and by further such application-dependent demands. If, for example, these measurement conditions change and the measurement principle should be expanded or converted for this reason or for another reason, a replacement of the complete measurement system is usually necessary. This is associated with a high cost effort and time effort and makes downtimes necessary.

A particular problem of optical apparatus for dust measurement lies in the fact that this apparatus is usually in direct contact with the dust-polluted environment. Consequently, deposits of dust can occur in practical use on the optical interfaces with which the apparatus is delimited with respect to the dust-polluted environment. It is therefore known from the prior art, for example from DE 1 993 225, to protect the optical interfaces against dust deposits by overpressure or, as in DE 29 31 266 C2, for example, to clean them with the aid of scavenging air. Depending on the measurement principle, however, there is a different scavenging air requirement so that each dust measurement device requires a scavenging air supply dimensioned for it. On the replacement of a dust measurement device, the scavenging air supply must therefore also be replaced, whereby the cost and/or effort is/are substantially increased.

Dust measurement devices are known in which the optical measuring head is accommodated in a housing and is connected to a connection unit which is located in a second housing and which has an integrated scavenging air supply. This connection unit is, however, designed for the measuring head associated with it, i.e. it is designed according to interfaces, evaluation and scavenging air requirement so that just the specific measuring head is supported with its measurement principle. On conversion to a different measurement principle, the connection unit must therefore also be replaced in addition to the sensor head.

Against this background, it is the object of the invention to provide a dust measurement system which allows a simple adaptation to changing measurement demands.

This object is satisfied by a modular dust measurement device in accordance with claim 1 and by a dust measurement method in accordance with claim 9. In this respect, the solution starts from the principle of providing the measuring heads in modular fashion with a uniform design and uniform interfaces and to provide a central module which allows the communication, evaluation and supply of a large family of sensor modules.

The solution in accordance with the invention has the advantage that a harmonized modular dust measurement system is provided which can be upgraded and retrofitted in a simple and cost-effective manner and which thereby becomes more future-proof. Adding on or upgrading is in part even possible in ongoing operation; installation in particular in power stations is substantially simplified. The complex and/or expensive complete replacement of all components with a temporary shutdown required in the prior art can thus be avoided. A harmonized functionality and operability means the system needs less servicing and is more user friendly. Finally, every single system per se also becomes more cost favorable in manufacture due to the harmonized design and fewer components have to be manufactured and stored.

The central module and the sensor module are advantageously each accommodated in a separate housing. Both modules are then protected and can be installed at a suitable location, for instance in that the central module is installed with better accessibility for operators with respect to the actual measurement location.

The central module preferably has some or all of the following connections: 0-20 mA power inputs and outputs, relays, digital inputs, PROFIBUS, Ethernet, CAN, serial, UMTS, GSM. It can thus be integrated in existing control installations, can transmit measurement data, can be polled wirelessly and can provide further devices to be connected with access to a power supply and to data networks.

The central module furthermore preferably has a memory device to record the input data of all connected sensor modules and to output them via a connection for evaluation, with the memory device in particular being removable and being insertable into an external computer or being connectable there. All relevant data can be recorded by this centralized logging function. The memory device can be removed for evaluations on a notebook or another computer so that one is not tied to the measurement location, particular for more complex evaluations or for test purposes of exhaust values.

The sensor modules of different measurement principles preferably include some or all of the following: transmission measurement devices, backscatter measurement devices with and without light trap, one-part forward scattered light measuring devices with lance-shaped measuring bodies or two-part forward scattered light measuring devices. The modular dust measurement in accordance with the invention can support all optical measuring heads in accordance with any desired measurement principles.

In a preferred further development, the sensor modules are also modular per se to allow the addition of further measurement functions or options. The modular design therefore also covers the design of the individual modules themselves. The manufacturing costs for the modules can thereby be kept low, on the one hand. In addition, it is thereby substantially facilitated to adapt the sensor modules to new tasks not by replacement, but by retrofitting. The central module can also have a modular design per se, for instance to provide additional connection positions for further sensor modules or new types of sensor module or to provide further functionality, for example for evaluation, data backup or operation.

The sensor modules among one another and with respect to the central module preferably have the same hardware and software structures, in particular the same processors, power supplies, interfaces, reset circuits, memory functions, status displays and/or firmware. The development, manufacture and maintenance is thus substantially simplified and more cost effective.

Uniform operating software is advantageously provided which enables the parameterization of the sensor modules, of the scavenging air and/or the display of measured data on a common display. The user thus only has to get used to the operating software once and can then make all settings and evaluations centrally without having to adapt to a new operating concept if, for instance, the sensor module is replaced or if other changes are made.

The method in accordance with the invention can be further developed in a similar manner and shows similar advantages. Such advantageous features are described in an exemplary, but not exclusive manner in the subordinate claims dependent on the independent claims.

Figure 2:
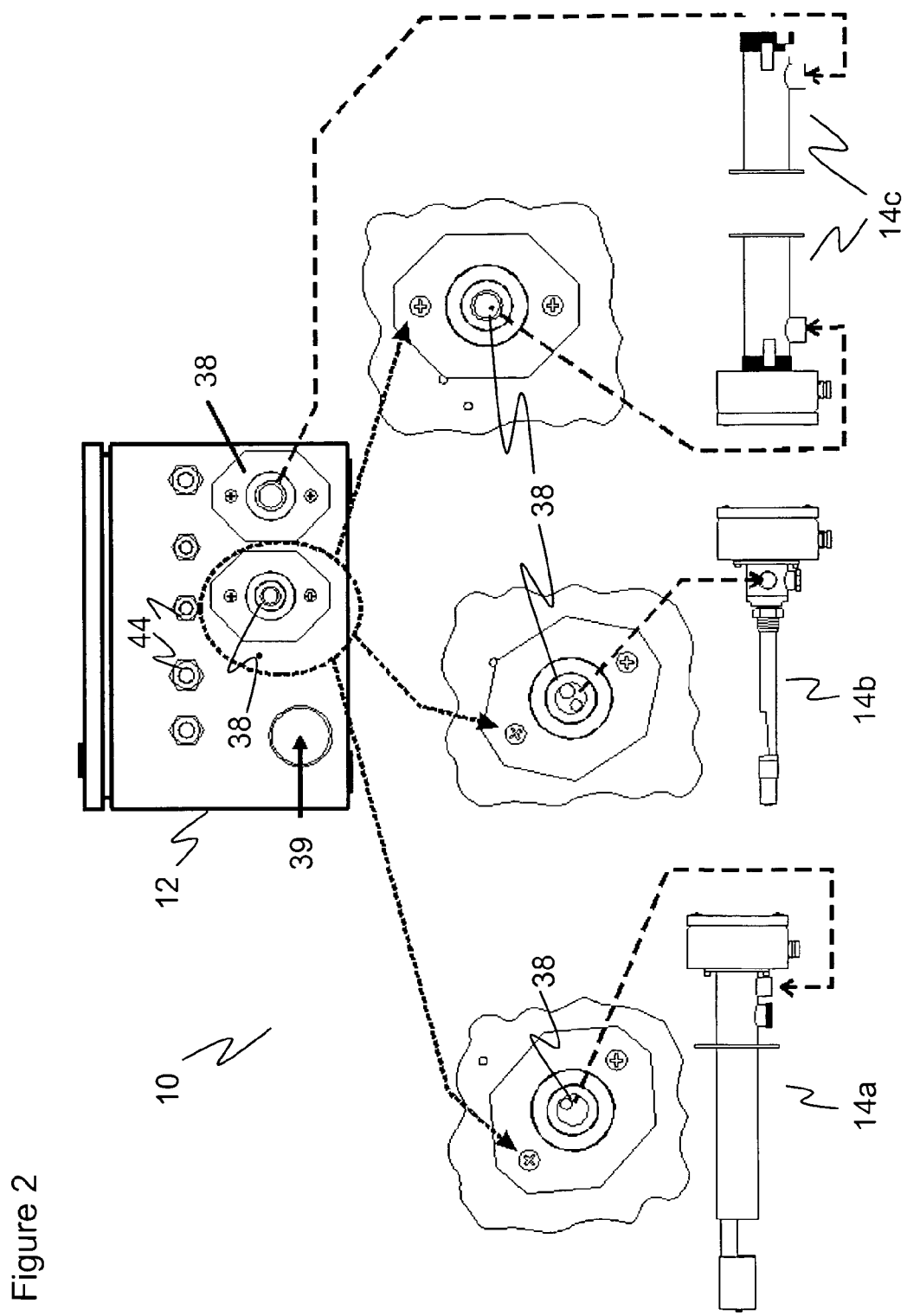

The invention will be explained in more detail in the following also with respect to further features and advantages by way of example with reference to embodiments and to the enclosed drawing. The Figures of the drawing show in:

FIG. 1 a schematic representation of the dust measurement system in accordance with the invention with a sensor module and the central module; and FIG. 2 a further schematic representation of the central module with a plurality of possible connectable sensor modules.

FIG. 1 shows a schematic representation of an embodiment of the modular dust apparatus 10 in accordance with the invention having a central module 12 and a sensor module 14. The sensor module 14 here works, by way of example, in accordance with the backscattering principle in that light of a light transmitter 16, for instance of a laser or of an LED, is transmitted into a measurement zone 18 and some of it is there scattered back at particles shown as a schematic cloud 20. The backscattered light is transformed into an electrical signal by a light receiver 22. A sensor control 24 is connected to the light transmitter 16 and the light receiver 24 to control the transmitted light and to receive the received signal.

The sensor control 24 outputs the received signal via a sensor interface 26. Either raw data or already preprocessed measurement results can be output in this respect. The data are brought into a standardized format for this purpose. The sensor interface 26 is connected to a corresponding central module interface 28. The interfaces 26, 28 utilize a fixed wired or wireless standard which is, however, any desired per se or a bus system.

The central module 12 has an evaluation unit 30 and a scavenging air unit 32. The evaluation unit 30 is connected to the central module interface 28 and thus receives the measurement data of the sensor module 14. A plurality of evaluation processes can be implemented in the evaluation unit 30 to process measurement data of different sensor modules 14.

The scavenging air unit 32 comprises a scavenging air control 34 connected to the evaluation unit 14 for the scavenging air management of the connected sensor modules 14, with the scavenging air management alternatively also being able to be integrated into the evaluation unit 30. The scavenging air unit furthermore comprises a fan 36 for the generation of an air flow which is made available at scavenging air connections 38. The fan 36 sucks in air via an air intake port 39 in the housing of the central module 12.

The sensor module 14 is connected to the scavenging air via a hose 40. The effective pressure and the scavenging air amount can be adapted to any connection 38 via different diameters of the connection pieces, also via valves or diaphragms, at the connections 38 and via an adjustment of the power consumption of the fan 36 by the scavenging air control 34. It is alternatively conceivable to operate the fan 36 at a fixed speed and to carry out the adaptation of the scavenging air only by the diameters of the connection pieces. Non-used connections 38 can be closed by a cap to maintain the pressure.

A memory device 42 is connected to the evaluation unit 30. It can be a card, but also another memory medium with a flash memory such as an SD card or a USB stick. The evaluation unit 30 stores measurement results and status information of the connected sensors 14 as well as operating parameters in the memory device 42, with the memory device 42 either being able to output these data via an interface 44 of the central module 12 or with the memory device 42 being removable as a whole and being able to be inserted into a computer for further evaluation.

A number of input/output functions are available to the user independently of the type of connected sensor module 14 via a plurality of interfaces and connections 44 connected to the evaluation unit 30. These connections can be supply connections or data interfaces, for instance 0-20 mA power inputs and power outputs, relays, digital inputs and outputs, PROFI- BUS, CAN, Ethernet, modem connection for remote data transfer and also wireless data interfaces such as UMTS, GSM or Bluetooth.

A display and operating element 46, for example a contact-sensitive LCD field, but also LEDs, buttons or combinations thereof, is provided at the central module 12. The user can view measurement data or carry out parameterization steps such as adjustments of the required scavenging air amount, but also visualization of maintenance demands or of the current measurement quality via this display and operating element 46 using a uniform man/machine interface independently of the sensor module 14 connected. The sensor modules 14 can keep required parameters stored themselves and report them to the central module 12; alternatively, also only transmit a type number or identification number to the evaluation unit 30 so that the required parameter set can be selected there.

Different sensor modules 14 are each provided in a housing with a uniform shape and coloring and a uniform manufacturing technology. The central module 12 also has a separate housing which can be uniform with those of the sensor modules 14. The sensor modules 14 have standard flanges for attachment to the gas passage.

Independently of the measurement principle, the same processor types, control functions, power supply, firmware and thus uniform hardware structures and software structures are used in the sensor modules 14 and in the central module 12. Sensor modules 14 are thus always completely compatible with one and the same universal central module 12 independently of the measurement principle. The modular principle is also continued in the design of the sensor modules 14 itself so that they can easily be extended or converted.

FIG. 2 shows the central module 12 and, by way of example, three connectable sensor modules 14a-14c. In this respect, the same reference numerals designate the same features as in FIG. 1. The connection 38 to the scavenging air takes place according to the demands of the measurement principle of the sensor module 14a-14c. Very little or little scavenging air is thus required for the measurement with forward scattering using a lance-shaped measuring body with the sensor modules 14a and 14b. On measurement of the transmission with a two-part sensor module 14c, both the reflector unit and the unit with light transmitter and light receiver have to be provided with scavenging air so that two connections 38 are required and there is a corresponding high demand for scavenging air.

The three sensor modules 14a-14c shown here are only examples for connectable sensor modules 14 using one of the optical principles such as have been described in the introduction. In this respect, one or more sensor modules 14 can be connected to a central module 12. In addition to the optical sensor modules 14, further dust-measuring modules 14 are also conceivable which work, for example, triboelectrically or gravimetrically. Other sensor modules 14 such as fire detectors or throughput measuring devices can also be connected to the central module 12 to utilize the uniform modular architecture, the interfaces and the operating concept.

The invention thus harmonizes the plurality of individual devices for dust measurement with optical measurement principles and integrates a complete product family with harmonized construction features, a modular structure, a uniform design, universal connection and evaluation electronics, uniform operating program and universal accessories. The user can thus adapt more cost-effectively and more flexibly to new demands of his applications.

The invention claimed is:

1. A modular dust measuring device for the determination of a foreign body concentration in a gas having at least one optical sensor head which has a light transmitter and a light receiver and having a central unit which has an evaluation unit and a scavenging air unit, further comprising:

the evaluation unit having a capability of determining the foreign body concentration with the help of a scattered light intensity or transmitted light intensity recorded by the light receiver and wherein the scavenging air unit can supply the sensor head with scavenging air to avoid or eliminate impurities or deposits; and the sensor head comprising a sensor module and the central unit comprising a central module, wherein the evaluation unit has a capability of evaluation and control of multiple sensor modules of different measurement principles, the sensor module interchangeably connected to the central module by standardized data interfaces and connections and the scavenging air unit having a configuration to make scavenging air available in the required quantity and with the required effective pressure for the multiple sensor modules of different measurement principles.

2. A dust measurement device in accordance with claim 1, wherein the central module and the sensor module are each accommodated in a separate housing.

3. A dust measurement device in accordance with claim 1, wherein the central module has a plurality of connections selected from the group comprising: 0-20 mA power inputs and outputs, relays, digital inputs, PROFIBUS, Ethernet, CAN, serial, UMTS, and GSM.

4. A dust measurement device in accordance with claim 1, wherein the central module has a memory device to record the input data of all connected sensor modules and to output them via a connection for evaluation, with the memory device in particular being removable and being insertable into an external commuter or being connectable there.

5. A dust measurement device in accordance with claim 1, wherein the sensor modules of different measurement principles include a plurality of sensor modules selected from the group consisting of: transmission measuring device, backscatter measuring device with and without light trap, one-part forward scattering light measuring device with lance-shaped measuring body and two-part forward scattered light measuring device.

6. A dust measurement device in accordance with claim 1, wherein the sensor modules are modular per se to enable the addition of further measurement functions or options.

7. A dust measurement device in accordance with claim 1, wherein the sensor modules have the same hardware structures and software structures among one another and/or with respect to the central module, in particular the same processors, power supplies, interfaces, reset circuits, memory functions, status displays and/or firmware.

8. A dust measurement device in accordance with claim 1, wherein uniform operating software is provided which enables the parameterization of the sensor modules, of the scavenging air and/or the display of measurement data on a common display.

9. A dust measurement method for the determination of a foreign body concentration in a gas by means of at least one optical sensor head which has a light transmitter and a light receiver, the method comprising:

determining the foreign body concentration in a central unit with the help of a scattered light intensity or transmitted light intensity recorded by the light receiver and providing the sensor head with scavenging air by the central unit to avoid or eliminate impurities or deposits; and using the central unit as a central module for the evaluation and control of sensor heads provided as multiple sensor modules of different measurement principles, with the central module and the sensor module interchangeably connected to one another by standardized data interfaces and connections and the central module providing the sensor module with scavenging air in the required quantity and with the required effective pressure.

10. A dust measuring method in accordance with claim 9, further comprising providing the sensor modules with the same hardware structures and software structures among one another and with respect to the central module for interchangeably connecting to the central module, in particular the same processors, power supplies, interfaces, reset circuits, memory functions, status displays and/or firmware, and/or with uniform operating software used to carry out the parameterization of the sensor modules, of the scavenging air and/or the display of measurement data on a common display.

* * * * *